(12) United States Patent
Liu et al.

(10) Patent No.: US 10,392,401 B2
(45) Date of Patent: Aug. 27, 2019

(54) CRYSTAL FORM A OF COMPOUND AND PREPARATION METHOD THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Jiang Wang, Shanghai (CN); Jian Li, Shanghai (CN); Jia Li, Shanghai (CN); Jingya Li, Shanghai (CN); Shengbin Zhou, Shanghai (CN); Mingbo Su, Shanghai (CN); Hualiang Jiang, Shanghai (CN); Xiaomin Luo, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/549,918

(22) PCT Filed: Feb. 3, 2016

(86) PCT No.: PCT/CN2016/073386
§ 371 (c)(1),
(2) Date: Aug. 9, 2017

(87) PCT Pub. No.: WO2016/127898
PCT Pub. Date: Aug. 18, 2016

(65) Prior Publication Data
US 2018/0030066 A1 Feb. 1, 2018

(30) Foreign Application Priority Data
Feb. 11, 2015 (CN) .......................... 2015 1 0073300

(51) Int. Cl.
*C07D 495/04* (2006.01)
*A61K 31/519* (2006.01)

(52) U.S. Cl.
CPC .......... *C07D 495/04* (2013.01); *A61K 31/519* (2013.01); *C07B 2200/13* (2013.01)

(58) Field of Classification Search
CPC .................................................. C07D 495/04
See application file for complete search history.

(56) References Cited

U.S. PATENT DOCUMENTS

| | | | | |
|---|---|---|---|---|
| 9,045,491 B2 * | 6/2015 | Liu | ....................... | C07D 495/04 |
| 2008/0300171 A1 | 12/2008 | Balkan et al. | | |
| 2014/0323466 A1 * | 10/2014 | Liu | ...................... | C07D 495/04 |
| | | | | 514/210.18 |

FOREIGN PATENT DOCUMENTS

| | | | |
|---|---|---|---|
| CN | 101817833 A | 9/2010 | |
| CN | 102659813 A | 9/2012 | |
| CN | 103130819 A | 6/2013 | |
| EP | 2 786 998 A1 | 10/2014 | |
| JP | 2015-500211 A | 1/2015 | |
| RU | 244014 C2 | 1/2012 | |
| WO | 2013/078765 A1 | 6/2013 | |
| WO | WO-2013078765 A1 * | 6/2013 | ........... C07D 495/04 |

OTHER PUBLICATIONS

Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*
Fathallah "Drug-Induced Hyperglycaemia and Diabetes" Drug Safety (2015) 38:1153-1168.*
Mayo Clinic Staff "Diseases and Conditions Chronic kidney disease" Jan. 30, 2015 Online " http://www.mayoclinic.org/diseasesconditions/kidneydisease/basics/causes/con2002677" accessed Dec. 11, 2015.*
Kumar et al. "Acute and chronic animal models for the evaluation of anti-diabetic agents" Cardiovascular Diabetology 2012, 11:9, 1-13.*
Baribault "Mouse Models of Type II Diabetes Mellitus in Drug Discovery" G. Proetzel, M.V. Wiles (eds.), Mouse Models for Drug Discovery, Methods in Molecular Biology 602, Humana Press, 2010, pp. 135-155.*
Rima Caccetta and Hani Al Salami "Screening for Antidiabetic Activities" Chapter 15 in Metabolomics Tools for Natural Product Discovery: Methods and Protocols, Methods in Molecular Biology, vol. 1055, 2013, pp. 207-218.*
Online "https://www.hopkinsguides.com/hopkins/view/Johns_Hopkins_Diabetes_Guide/547042/all/DPP_IV_Inhibitors" accessed Dec. 7, 2018.*
Vickers "The utility of animal models to evaluate novel anti-obesity agents" British Journal of Pharmacology (2011) 164 1248-1262.*
Lutz "Overview of Animal Models of Obesity" Curr Protoc Pharmacol. Sep. 2012; Chapter: Unit 5.61. 1-22.*
"The Practical Guide Identification, Evaluation, and Treatment of Overweight and Obesity in Adults" NIH Publication No. 00-4084 Oct. 2000.*
International Search Report (English translation) corresponding to PCT/CN2016/073386 dated May 10, 2016 (2 pages).
Extended European Search Report corresponding to PCT/CN2016/073386 dated Jun. 27, 2018 (5 pages).
Notification of Reason for Refusal for corresponding Appl 1020177024861 in the Republic of Korea issued by KIPO dated Sep. 17, 2018 (English Translation); 4 pages.

(Continued)

*Primary Examiner* — David K O'Dell
(74) *Attorney, Agent, or Firm* — Mintz Levin Cohn Ferris Glovsky and Popeo PC

(57) ABSTRACT

The present invention relates to crystal form A of a compound. The present invention also discloses a preparation method and a pharmaceutical composition of the crystal form A. The crystal form A has strong hypoglycemic activity in vivo and is expected to be a novel pharmaceutically active ingredient for treating or preventing type II diabetes and/or complications of type II diabetes.

9 Claims, 4 Drawing Sheets

(56) References Cited

OTHER PUBLICATIONS

Report on First Office Action for corresponding Appl 2017130691 in the Russian Federation dated Sep. 24, 2018 (English); 2 pages.
Hirayama, Noriaki, "Organic Compound Crystal Production Handbook Principle and Know-How," *Maruzen Co., Ltd.* (Jul. 25, 2018); pp. 17-23; 37-40; 45-51; 57-65.
Matsuoka, Masakuni, "Advanced Crystallization Technology of Organic Materials—Control of Size, Morphology, Polymorph and Purity," *PHARM TECHJAPAN* (May 1, 2003); vol. 19, No. 6, pp. 91-101; see, English language abstract, p. 1.
MHW Pharmaceutical Safety Bureau Evaluation and Licensing Division, "Drug Residue Guidelines," *Japanese Pharmaceutical Trial* (1998); No. 307, pp. 1-11.
Report on First Office Action for corresponding Appl 2017-542114 in Japan issued by JPO dated Jun. 6, 2018 (English Translation); 4 pages.
Shioji, Yusoh,, "Manufacturing Technology of Solid Preparation," *Tokyo: CMC Publishing* (Jan. 27, 2003); pp. 9, 12-13.
Takada, Noriyuki, "Drug substance form screening and selection of drug substance," *PHARM Stage* (Jan. 15, 2007); vol. 6, No. 10, pp. 20-25.

\* cited by examiner

CRYSTAL FORM A OF COMPOUND AND PREPARATION METHOD THEREOF

TECHNICAL FIELD

The present invention relates to the field of pharmaceutical chemistry, and more particularly to crystal form A of (R)-methyl-2-(3-aminopiperidin-1-yl)-3-(2-cyanobenzyl)-4-carbonyl-3,4-dihydrothiop hene[3,2-d]pyrimidine-6-carboxylic acid crystal and preparation method thereof.

BACKGROUND ART

Diabetes Mellitus (DM) is a metabolic disease of multiple causes, and is a syndrome of a series of metabolism disorder of protein, fat, water, electrolytes and the like caused by absolute or relative lack of insulin secretion in the human body or reduced sensitivity of target cells to insulin. Acute complications of diabetes include diabetic ketoacidosis, diabetic hyperosmolar coma, a variety of acute infection and lactic acidosis and so on. In addition, hypoglycemia existed in the treatment of diabetes is also one of the most common acute complications. Chronic complications of diabetes include diabetic eye disease, diabetic nephropathy, diabetic neuropathy, diabetic heart and brain limbs macrovascular disease and diabetic foot and skin lesions etc.

Type II diabetes is a type of metabolic syndrome caused by uncontrolled blood glucose levels in vivo. Type II diabetes is characterized by high blood glucose, insulin resistance and lack of insulin secretion, and is usually associated with dyslipidemia, hypertension and obesity. Type II diabetes is a global epidemic, and all over the world 6% of the population are currently suffering from type II diabetes, which has become the world's third chronic non-communicable diseases threatening human health. Type II diabetes patients can produce insulin in the human body, but the quantity is relative insufficient, or the obtained insulin can not function effectively due to reduced tissue sensitivity or insulin resistance, so glucose accumulates in blood and glucose level is increased. Since this type of diabetes patients can secrete insulin, insulin therapy is generally not needed, and blood glucose can be controlled only by diet adjustment or oral hypoglycemic agents.

In 2000, there were about 171 million diabetics in the world. It is expected that if there is no effective treatment, in 2030, the number of diabetics will reach 360 million, of which more than 90% are type II diabetes. In China, diabetes treatment costs up to 173.4 billion RMB per year, diabetes-induced direct medical expenses have accounted for 13% of China's total medical expenditure. It is expected that the number of diabetic patients in the United States will reach 50 million in 2028 with an annual growth rate of 5%. While in China the number of diabetes patients up to 92.5 million now is expected to reach 100 million in 2028 with an annual growth rate of 4%. As a complex disease, type II diabetes patients have strong heterogeneity, and Easterners have a higher susceptibility to type II diabetes than Westerners, and demand for individualized treatment is high.

Current drugs for treating type II diabetes mainly include insulin, sulfonylureas, metformin, thiazolidinediones, PPARα/γ double agonists, DPP IV inhibitors and GLP-1 analogs. Although the existing drugs can control blood glucose levels and reduce the occurrence of complications, but most of them have more serious side effects, such as gastrointestinal toxicity, weight gain, edema, hypoglycemia and the like, and they can not fundamentally control and cure type II diabetes. Since traditional diabetes treatment drugs have limited effect and poor tolerance as well as obvious side effects, from the perspective of human health and economic interests, it has important research significance to research and develop safe and highly efficient diabetes treatment drugs.

DPP IV inhibitors can significantly reduce blood glucose levels in the body, increase glucose tolerance, promote insulin secretion, reduce glucagon level, delay insulin resistance and increase response level of insulin when blood glucose increases in patients with type II diabetes. Compared with existing oral diabetes drugs, DPP IV inhibitors have following characteristics: (1) DPP IV inhibitors do not require injections, and continuously reduce glycosylated hemoglobin level by oral administration; (2) DPP IV inhibitors have good tolerance after long-term use; (3) DPP IV inhibitors can enhance insulin secretion and improve the release of glucagon; (4) DPP IV inhibitors improve insulin sensitivity and increase pancreatic β cell function; (5) lower incidence of hypoglycemia, and it will not cause weight gain, nausea and vomiting and gastrointestinal dysfunction; (6) DPP IV inhibitors have synergistic effects when they are used with other type II diabetes drugs.

(R)-methyl-2-(3-aminopiperidin-1-yl)-3-(2-cyanobenzyl)-4-carbonyl-3,4-dihydroth iophene[3,2-d] pyrimidine-6-carboxylic acid (Formula I) is a novel DPP IV inhibitor with strong activity of reducing blood glucose in vivo. However, the overall performance of the existing various crystalline forms of (R)-methyl-2-(3-aminopiperidin-1-yl)-3-(2-cyanobenzyl)-4-carbonyl-3,4-dihydrothiop hene[3,2-d] pyrimidine-6-carboxylic acid is still unsatisfactory.

Therefore, there is an urgent need in the art for the development of a new crystal form of (R)-methyl-2-(3-aminopiperidin-1-yl)-3-(2-cyanobenzyl)-4-carbonyl-3,4-dihydrothiop hene[3,2-d] pyrimidine-6-carboxylic acid with high efficiency, low toxicity and long-lasting effect so as to obtain a pharmaceutically active ingredient with better performance.

SUMMARY OF INVENTION

One object of the present invention is to provide crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal with high efficiency, low toxicity and long-lasting effect.

In the first aspect of the present invention, crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal of formula I is provided, XRD pattern of the crystal form A includes following characteristic absorption peaks expressed by crystal plane distance d: 8.87±0.2 Å, 14.18±0.2 Å, 20.67±0.2 Å, 25.18±0.2 Å, 28.61±0.2 Å.

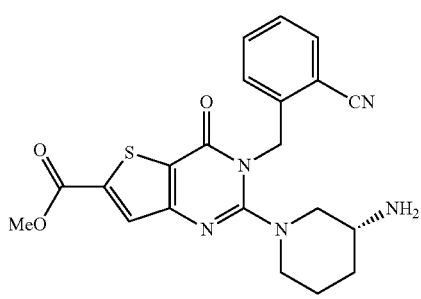

I

In another preferred embodiment, the XRD pattern of the crystal form A includes following characteristic absorption peaks expressed by crystal plane distance d: 8.87 Å, 14.18 Å, 20.67 Å, 25.18 Å, 28.61 Å.

In another preferred embodiment, the XRD pattern of the crystal form A includes following characteristic absorption peaks expressed by crystal plane distance d: 7.25±0.2 Å, 8.09±0.2 Å, 8.87±0.2 Å, 14.18±0.2 Å, 16.65±0.2 Å, 20.67±0.2 Å, 21.95±0.2 Å, 25.18±0.2 Å, 28.61±0.2 Å.

In another preferred embodiment, the XRD pattern of the crystal form A includes following characteristic absorption peaks expressed by crystal plane distance d: 7.25 Å, 8.09 Å, 8.87 Å, 14.18 Å, 16.65 Å, 20.67 Å, 21.95 Å, 25.18 Å, 28.61 Å.

In another preferred embodiment, the XRD pattern of the crystal form A includes following characteristic absorption peaks expressed by crystal plane distance d: 7.25±0.2 Å, 8.09±0.2 Å, 8.87±0.2 Å, 14.18±0.2 Å, 16.65±0.2 Å, 19.03±0.2 Å, 20.01±0.2 Å, 20.67±0.2 Å, 21.95±0.2 Å, 24.53±0.2 Å, 25.18±0.2 Å, 27.47±0.2 Å, 28.61±0.2 Å.

In another preferred embodiment, the XRD pattern of the crystal form A includes following characteristic absorption peaks expressed by crystal plane distance d: 7.25 Å, 8.09 Å, 8.87 Å, 14.18 Å, 16.65 Å, 19.03 Å, 20.01 Å, 20.67 Å, 21.95 Å, 24.53 Å, 25.18 Å, 27.47 Å, 28.61 Å.

In another preferred embodiment, the XRD pattern of the crystal form A includes following characteristic absorption peaks expressed by crystal plane distance d: 5.42±0.2 Å, 7.25±0.2 Å, 8.09±0.2 Å, 8.87±0.2 Å, 14.18±0.2 Å, 15.59±0.2 Å, 16.65±0.2 Å, 17.84±0.2 Å, 19.03±0.2 Å, 20.01±0.2 Å, 20.67±0.2 Å, 21.72±0.2 Å, 21.95±0.2 Å, 22.49±0.2 Å, 24.53±0.2 Å, 25.18±0.2 Å, 25.56±0.2 Å, 27.47±0.2 Å, 28.61±0.2 Å, 33.09±0.2 Å, 34.25±0.2 Å, 37.86±0.2 Å.

In another preferred embodiment, the XRD pattern of the crystal form A includes following characteristic absorption peaks expressed by crystal plane distance d: 5.42 Å, 7.25 Å, 8.09 Å, 8.87 Å, 14.18 Å, 15.59 Å, 16.65 Å, 17.84 Å, 19.03 Å, 20.01 Å, 20.67 Å, 21.72 Å, 21.95 Å, 22.49 Å, 24.53 Å, 25.18 Å, 25.56 Å, 27.47 Å, 28.61 Å, 33.09 Å, 34.25 Å, 37.86 Å.

In another preferred embodiment, the crystal form A has an XRD pattern substantially as shown in FIG. 2.

In another preferred embodiment, the characteristic absorption peak expressed by crystal plane distance d of the XRD pattern of the crystal form A has a deviation of ±0.5, preferably a deviation of ±0.3, and more preferably a deviation of ±0.1.

In another preferred embodiment, the crystal form A has one or more characteristics selected from the following group consisting of:

1) TG pattern of the crystal form A has a characteristic absorption peak at 261±2° C.;

In another preferred embodiment, the TG pattern of the crystal form A has a characteristic absorption peak at 262.1° C.

2) TG pattern of the crystal form A has a characteristic absorption peak at 323±5° C.;

In another preferred embodiment, the TG pattern of the crystal form A has a characteristic absorption peak at 324° C.

3) the crystal form A has a heat weight loss of 77 to 78 wt % at 400° C.;

In another preferred embodiment, the crystal form A has a heat weight loss of 77.65 wt % at 400° C.

In another preferred embodiment, the crystal form A has a TG pattern substantially as shown in FIG. 3.

4) DSC pattern of the crystal form A has a characteristic absorption peak at 135±5° C.;

In another preferred embodiment, the DSC pattern of the crystal form A has a characteristic absorption peak at 135.67° C.

In another preferred embodiment, a starting value of an endothermic transition temperature of the crystal form A is 131±2° C.

In another preferred embodiment, the starting value of the endothermic transition temperature of the crystal form A is 131.84° C.

In another preferred embodiment, the crystal form A has a DSC pattern substantially as shown in FIG. 4.

5) the crystal form A has a hygroscopicity of less than 1%.

In another preferred embodiment, when relative humidity RH is less than 50%, the crystal form A has a hygroscopicity of less than 0.3%.

In another preferred embodiment, the crystal form A has a DVS pattern substantially as shown in FIG. 5.

In another preferred embodiment, IR pattern of the crystal form A includes following characteristic absorption peaks expressed by wavelength λ: 3368±2 $cm^{-1}$, 2940±2 $cm^{-1}$, 2848±2 $cm^{-1}$, 2222±2 $cm^{-1}$, 1729±2 $cm^{-1}$, 1672±2 $cm^{-1}$, 1564±2 $cm^{-1}$, 1529±2 $cm^{-1}$, 1470±2 $cm^{-1}$, 1454±2 $cm^{-1}$, 1387±2 $cm^{-1}$, 1298±2 $cm^{-1}$, 1203±2 $cm^{-1}$, 1105±2 $cm^{-1}$, 1075±2 $cm^{-1}$, 921±2 $cm^{-1}$, 781±2 $cm^{-1}$, 709±2 $cm^{-1}$.

In another preferred embodiment, IR pattern of the crystal form A includes following characteristic absorption peaks expressed by wavelength λ: 3368, 2940, 2848, 2222, 1729, 1672, 1564, 1529, 1470, 1454, 1387, 1298, 1203, 1105, 1075, 921, 781, 709 $cm^{-1}$.

In another preferred embodiment, the crystal form A has an IR pattern substantially as shown in FIG. 6.

In another preferred embodiment, the crystal form A has a Raman pattern substantially as shown in FIG. 7.

In the second aspect of the present invention, a crystal composition is provided, and it comprises a crystal of the crystal form A according to the first aspect of the present invention or is made from a crystal of the crystal form A according to the first aspect of the present invention.

In another preferred embodiment, the weight percentage of the crystal of the crystal form A is 60 to 99.999%, preferably 80 to 99.999%, more preferably 90 to 99.999%, based on total weight of the crystal composition, In another preferred embodiment, the crystal composition further comprises: non-A crystal form of (R)-methyl-2-(3-aminopiperidin-1-yl)-3-(2-cyanobenzyl)-4-carbonyl-3,4-dihydrothiophene[3,2-d] pyrimidine-6-carboxylic acid crystal and amorphous (R)-methyl-2-(3-aminopiperidin-1-yl)-3-(2-cyanobenzyl)-4-carbonyl-3,4-dihydrothiophene[3,2-d] pyrimidine-6-carboxylic acid.

In the third aspect of the present invention, it provides a method for preparing the crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal according to the first aspect of the present invention, and the method comprises following steps:

1) providing a first solution containing a first solvent and (R)-methyl-2-(3-aminopiperidin-1-yl)-3-(2-cyanobenzyl)-4-carbonyl-3,4-dihydrothiophene[3,2-d] pyrimidine-6-carboxylic acid dissolved in the first solvent, wherein the first solvent is a good solvent and selected from the following group consisting of alcohols, ketones, esters, chlorinated alkanes, or combinations thereof;

In another preferred embodiment, the alcohols are C1-C10 alcohols, preferably C1-C8 alcohols, more preferably C1-05 alcohols.

In another preferred embodiment, the alcohols are selected from the following group consisting of methanol, ethanol, n-propanol, isopropanol, n-butanol, neopentyl alcohol, or combinations thereof.

In another preferred embodiment, the ketones are C2-C8 ketones, preferably C3-C5 ketones.

In another preferred embodiment, the ketones are selected from the following group consisting of acetone, isobutanol butanone, or combinations thereof.

In another preferred embodiment, the esters are C1-C10 esters, preferably C1-C7 esters, more preferably C1-C5 esters.

In another preferred embodiment, the esters are selected from the following group consisting of methyl formate, ethyl acetate, isobutyl formate, or combinations thereof.

In another preferred embodiment, the chlorinated alkanes are dichloromethane, trichloromethane, or combinations thereof, preferably dichloromethane.

In another preferred embodiment, the (R)-methyl-2-(3-aminopiperidin-1-yl)-3-(2-cyanobenzyl)-4-carbonyl-3,4-dihydrothiop hene[3,2-d] pyrimidine-6-carboxylic acid is an amorphous compound.

2) adding a second solvent to the first solution to crystallize and give the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal according to the first aspect of the present invention, wherein
the second solvent is a poor solvent and selected from the following group consisting of water, ethers, alkanes, tetrahydrofuran, 1,4-dioxane, or combinations thereof.

In another preferred embodiment, the ethers are C1-C10 ethers, preferably C1-C8 ethers, more preferably C1-C6 ethers.

In another preferred embodiment, the ethers are selected from the following group consisting of petroleum ether, t-butyl methyl ether, diethyl ether, isopropyl ether, diethyl ether, or combinations thereof.

In another preferred embodiment, the alkanes are C2-C15 alkanes, preferably C3-C10 alkanes, more preferably C4-C8 alkanes.

In another preferred embodiment, the alkanes are selected from the following group consisting of n-pentane, n-hexane, n-heptane, or combinations thereof.

In another preferred embodiment, after step 2), the method further comprises the following step:

(3) filtering and/or drying the obtained solid in step (2), to give the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal according to the first aspect of the present invention.

In another preferred embodiment, temperature for the drying is from 10 to 70° C., preferably from 20 to 80° C., more preferably from 25 to 40° C.

In another preferred embodiment, pressure for the drying is from 0 to 20 kPa, preferably from 0 to 10 kPa, more preferably from 5 to 10 kPa.

In another preferred embodiment, time for the drying is from 5 to 150 hours, preferably from 30 to 100 hours, more preferably from 60 to 80 hours.

In another preferred embodiment, the yield of the method is from 50% to 99%, preferably from 75% to 99%, more preferably from 85% to 99%.

In another preferred embodiment, in the first solution, the concentration of the solute (R)-methyl-2-(3-aminopiperidin-1-yl)-3-(2-cyanobenzyl)-4-carbonyl-3,4-dihydrothiop hene[3,2-d] pyrimidine-6-carboxylic acid is 0.1 g/L to the saturated concentration.

In another preferred embodiment, in the first solution, the concentration of the solute (R)-methyl-2-(3-aminopiperidin-1-yl)-3-(2-cyanobenzyl)-4-carbonyl-3,4-dihydrothiop hene [3,2-d] pyrimidine-6-carboxylic acid is 0.1 g/L to 100 g/L, preferably 1 g/L to 870 g/L, more preferably 10 g/L to 70 g/L, most preferably 10 g/L to 50 g/L.

In another preferred embodiment, in the first solution, the concentration of the solute (R)-methyl-2-(3-aminopiperidin-1-yl)-3-(2-cyanobenzyl)-4-carbonyl-3,4-dihydrothiop hene [3,2-d] pyrimidine-6-carboxylic acid is an unsaturated concentration.

In another preferred embodiment, the crystallization is carried out at 0 to 50° C.

In another preferred embodiment, the crystallization is carried out at 0 to 40° C., preferably 20 to 30° C.; preferably room temperature.

In another preferred embodiment, the crystallization is carried out with stirring.

In the fourth aspect of the present invention, a pharmaceutical composition is provided, comprising the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal according to the first aspect of the present invention, and pharmaceutically acceptable excipients.

In another preferred embodiment, the excipient is selected from the following group consisting of fillers, disintegrants, binders, lubricants, or combinations thereof.

In another preferred embodiment, the filler is selected from the following group consisting of starch, lactose, microcrystalline cellulose, dextrin, mannitol, magnesium oxide, calcium sulfate, or combinations thereof.

In another preferred embodiment, the disintegrant is selected from the following group consisting of carboxymethylcellulose and salts thereof, crosslinked carboxymethylcellulose and salts thereof, crosslinked povidone, sodium carboxymethyl starch, low substituted hydroxypropylcellulose, or combinations thereof.

In another preferred embodiment, the binder is selected from the following group consisting of povidone, hydroxypropylmethylcellulose, starch pulp, or combinations thereof.

In another preferred embodiment, the lubricant is selected from the following group consisting of magnesium stearate, calcium stearate, or combinations thereof.

In the fifth aspect of the present invention, a use of the crystal form A of (R)-methyl-2-(3-aminopiperidin-1-yl)-3-(2-cyanobenzyl)-4-carbonyl-3,4-dihydrothiophene [3,2-d] pyrimidine-6-carboxylic acid crystal according to the first aspect of the present invention or the crystal composition according to the second aspect of the present invention or the pharmaceutical composition according to fourth aspect of the present invention is provided, for preparation of a medicament for preventing or treating type II diabetes and/or complications of type II diabetes.

In another preferred embodiment, the complications of type II diabetes are selected from the following group consisting of coronary artery disease, stroke, hypertension, nephropathy, peripheral vascular disease, neurological disease, and retinopathy.

In the sixth aspect of the present invention, it provides a method of treating or preventing type II diabetes and/or complications of type II diabetes, by administering to a subject a therapeutically effective amount of the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal according to the first aspect of the present invention or the crystal composition according to the second aspect of the present invention or the pharmaceutical composition according to fourth aspect of the present invention.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Figure 1:
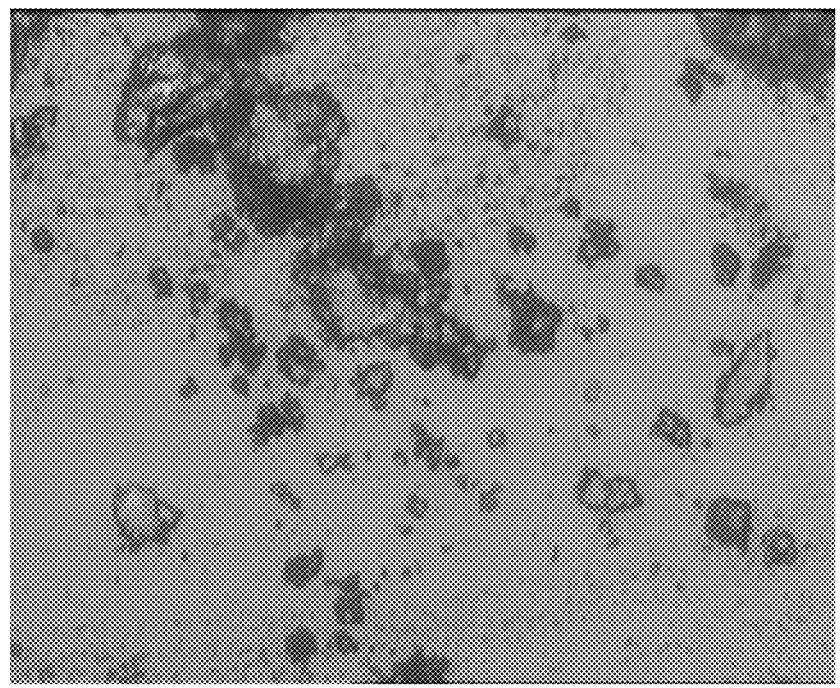
FIG. 1 is a polarizing photograph of the crystal form A of the crystal of Example 1 of the present invention.

Through extensive and intensive long research, the inventors have unexpectedly prepared crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal with better pharmaceutical properties. Based on the above findings, the inventors have completed the present invention.

Amorphous Powder (R)-methyl-2-(3-aminopiperidin-1-yl)-3-(2-cyanobenzyl)-4-carbonyl-3,4-dihydroth iophene[3,2-d] pyrimidine-6-carboxylic acid (Formula I) is a novel DPP IV inhibitor with strong activity for reducing blood glucose in vivo. The compound is a selective and reversible competitive DPP IV inhibitor with an inhibitory activity up to nanomolar level, and the inhibitory activity and selectivity of DPP IV inhibitors in vitro is superior to those of listed drugs sitagliptin and vildagliptin. In animal body, the compound can effectively inhibit DPP IV activity in normal mice and rat plasma, and its DPP IV inhibitory activity is superior to that of listed drug alogliptin. The compound can increase oral glucose tolerance in normal ICR mice in dose-dependent manner with an effective dose of only 0.1 mg/kg, and its effect is superior to that of alogliptin. When the compound is chronicly administered to ob/ob mice, it can effectively reduce fasting blood glucose of ob/ob mice, which is superior to the positive control drug alogliptin. When the compound is chronicly administered to gene-deficient db/db mice, it can reduce fasting blood glucose of gene-deficient db/db mice, which is comparable to the positive control drug alogliptin. Study of pharmacokinetic and safety has shown that the compound has good pharmacokinetic properties and safety in rats and dogs. In rats and dogs, half-life and $AUC_{0-t}$ of the compound is superior to those of listed drug alogliptin. Safety test has showed that the compound has good safety, and the acute toxicity test in ICR mice has showed that no death is found in 300 mg/kg group, and the acute toxicity test in Beagles has showed that no death is found in 1 g/kg group, and the subacute toxicity test in Rat has showed that no obvious toxicity is found in oral administrated 150 mg/kg group. Summarizing research results of pharmacodynamics evaluation in vitro, pharmacological evaluation in vivo, pharmacokinetic studies and safety evaluation etc., hypoglycemic effect of the compound in vivo is better than that of DPPIV inhibitors currently clinically used. Therefore, the compound is expected to develop as a novel therapeutic agent for Type II diabetes.

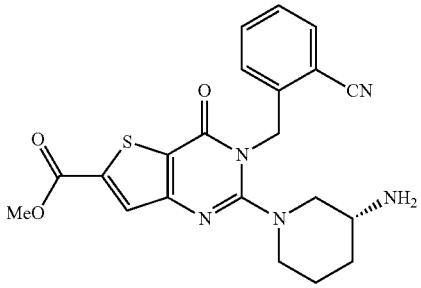

I

Drug Polymorphism refers to the drug has two or more material states in different crystalline forms. For solid chemical drugs, due to their different molecular arrangement and symmetry laws, one drug can form a variety of solid material states in different crystalline form, and it is often referred to as "polymorph phenomenon" that one drug has solid states in different crystalline forms. Polymorph phenomenon is prevalent in solid drugs, and polymorph is one of important factors that affect quality and efficacy of solid drugs.

Amorphous (R)-methyl-2-(3-aminopiperidin-1-yl)-3-(2-cyanobenzyl)-4-carbonyl-3,4-dihydrothiop hene[3,2-d] pyrimidine-6-carboxylic acid powder is prepared by the preparation method described in patent application no. CN201210262331.3. $^1$H NMR(CDCl$_3$): δ 7.76(s, 1H), 7.610 (d, 1H), 7.493 (t, 1H), 7.320 (t, 1H), 7.180 (d, 1H), 5.500 (quartet, 2H), 3.895 (s, 3H), 3.680 (d, 2H), 3.355 (m, 1H), 3.010 (m, 2H), 2.150 (m, 1H), 1.894 (m, 2H), 1.644 (m, 1H); LC-MS m/z 424.1 [M+H]$^+$.

Crystal Form A

Crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal of formula I is provided in the present invention, XRD pattern of the crystal form A includes following characteristic absorption peaks expressed by crystal plane distance d: 8.87±0.2 Å, 14.18±0.2 Å, 20.67±0.2 Å, 25.18±0.2 Å, 28.61±0.2 Å.

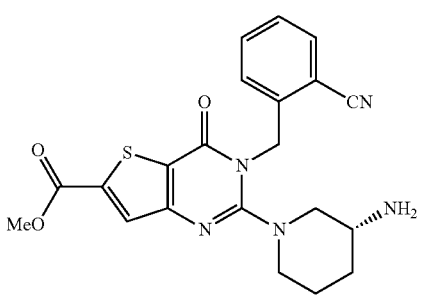

I

In another preferred embodiment, the XRD pattern of the crystal form A includes following characteristic absorption peaks expressed by crystal plane distance d: 8.87 Å, 14.18 Å, 20.67 Å, 25.18 Å, 28.61 Å.

Typically, the XRD pattern of the crystal form A includes following characteristic absorption peaks expressed by crystal plane distance d: 7.25±0.2 Å, 8.09±0.2 Å, 8.87±0.2 Å, 14.18±0.2 Å, 16.65±0.2 Å, 20.67±0.2 Å, 21.95±0.2 Å, 25.18±0.2 Å, 28.61±0.2 Å.

In another preferred embodiment, the XRD pattern of the crystal form A includes following characteristic absorption peaks expressed by crystal plane distance d: 7.25 Å, 8.09 Å, 8.87 Å, 14.18 Å, 16.65 Å, 20.67 Å, 21.95 Å, 25.18 Å, 28.61 Å.

In another preferred embodiment, the XRD pattern of the crystal form A includes following characteristic absorption peaks expressed by crystal plane distance d: 7.25±0.2 Å, 8.09±0.2 Å, 8.87±0.2 Å, 14.18±0.2 Å, 16.65±0.2 Å, 19.03±0.2 Å, 20.01±0.2 Å, 20.67±0.2 Å, 21.95±0.2 Å, 24.53±0.2 Å, 25.18±0.2 Å, 27.47±0.2 Å, 28.61±0.2 Å.

In another preferred embodiment, the XRD pattern of the crystal form A includes following characteristic absorption peaks expressed by crystal plane distance d: 7.25 Å, 8.09 Å, 8.87 Å, 14.18 Å, 16.65 Å, 19.03 Å, 20.01 Å, 20.67 Å, 21.95 Å, 24.53 Å, 25.18 Å, 27.47 Å, 28.61 Å.

In another preferred embodiment, the XRD pattern of the crystal form A includes following characteristic absorption peaks expressed by crystal plane distance d: 5.42±0.2 Å, 7.25±0.2 Å, 8.09±0.2 Å, 8.87±0.2 Å, 14.18±0.2 Å, 15.59±0.2 Å, 16.65±0.2 Å, 17.84±0.2 Å, 19.03±0.2 Å, 20.01±0.2 Å, 20.67±0.2 Å, 21.72±0.2 Å, 21.95±0.2 Å, 22.49±0.2 Å, 24.53±0.2 Å, 25.18±0.2 Å, 25.56±0.2 Å, 27.47±0.2 Å, 28.61±0.2 Å, 33.09±0.2 Å, 34.25±0.2 Å, 37.86±0.2 Å.

In another preferred embodiment, the XRD pattern of the crystal form A includes following characteristic absorption peaks expressed by crystal plane distance d: 5.42 Å, 7.25 Å, 8.09 Å, 8.87 Å, 14.18 Å, 15.59 Å, 16.65 Å, 17.84 Å, 19.03 Å, 20.01 Å, 20.67 Å, 21.72 Å, 21.95 Å, 22.49 Å, 24.53 Å, 25.18 Å, 25.56 Å, 27.47 Å, 28.61 Å, 33.09 Å, 34.25 Å, 37.86 Å.

Figure 2:
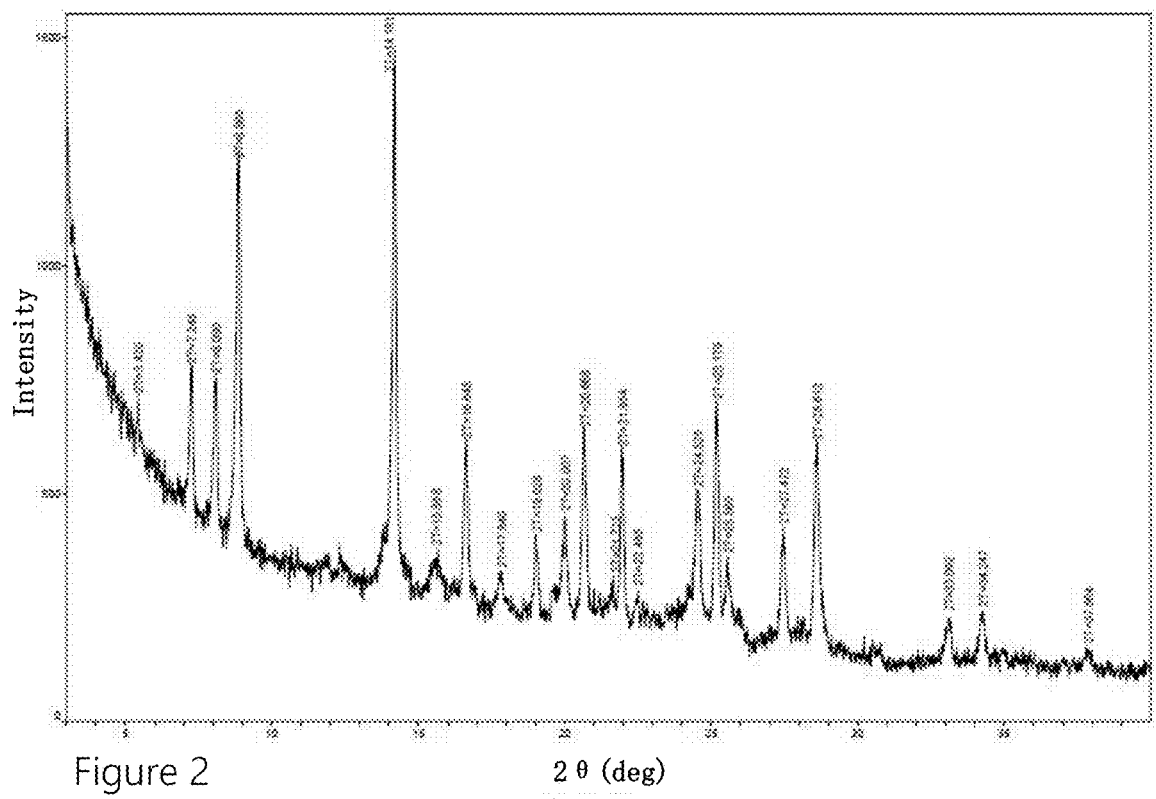
FIG. 2 is an XRD pattern of the crystal form A of the crystal of Example 1 of the present invention.

In another preferred embodiment, the crystal form A has an XRD pattern substantially as shown in FIG. 2.

In the present invention, the characteristic absorption peak expressed by crystal plane distance d in the XRD pattern of the crystal form A has a deviation of ±0.5, preferably a deviation of ±0.3, and more preferably a deviation of ±0.1.

Specifically, the crystal form A has one or more characteristics selected from the following group consisting of:

1) TG pattern of the crystal form A has a characteristic absorption peak at 261±2° C.;

In another preferred embodiment, the TG pattern of the crystal form A has a characteristic absorption peak at 262.1° C.

2) TG pattern of the crystal form A has a characteristic absorption peak at 323±5° C.;

In another preferred embodiment, the TG pattern of the crystal form A has a characteristic absorption peak at 324° C.

3) the crystal form A has a heat weight loss of 77 to 78 wt % at 400° C.;

In another preferred embodiment, the crystal form A has a heat weight loss of 77.65 wt % at 400° C.

Figure 3:
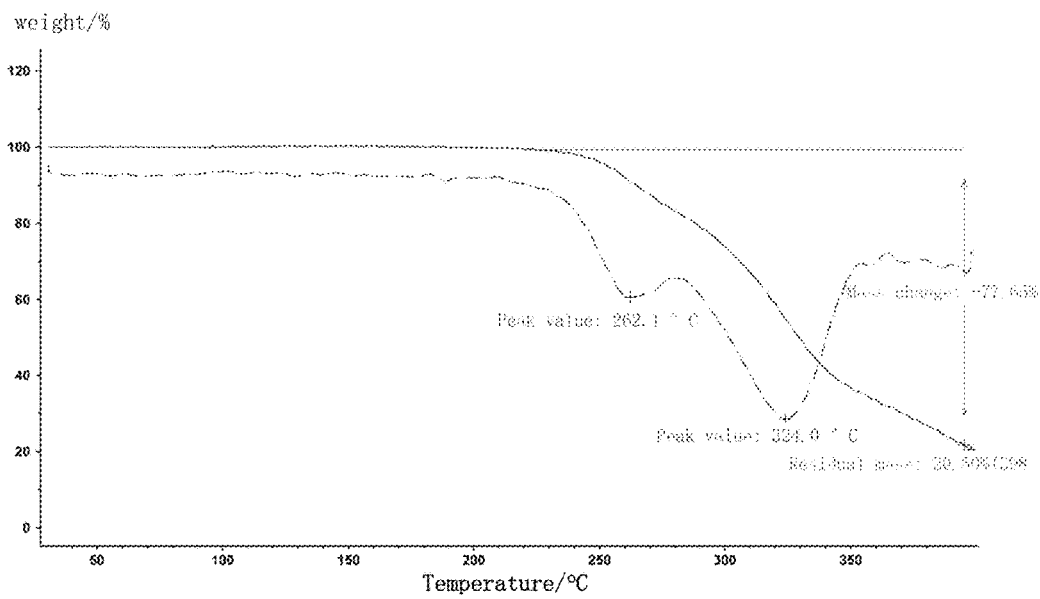
FIG. 3 is a TG pattern of the crystal form A of the crystal of Example 1 of the present invention.

In another preferred embodiment, the crystal form A has a TG pattern substantially as shown in FIG. 3.

4) DSC pattern of the crystal form A has a characteristic absorption peak at 135±5° C.;

In another preferred embodiment, the DSC pattern of the crystal form A has a characteristic absorption peak at 135.67° C.

In another preferred embodiment, a starting value of an endothermic transition temperature of the crystal form A is 131±2° C.

In another preferred embodiment, the starting value of the endothermic transition temperature of the crystal form A is 131.84° C.

Figure 4:
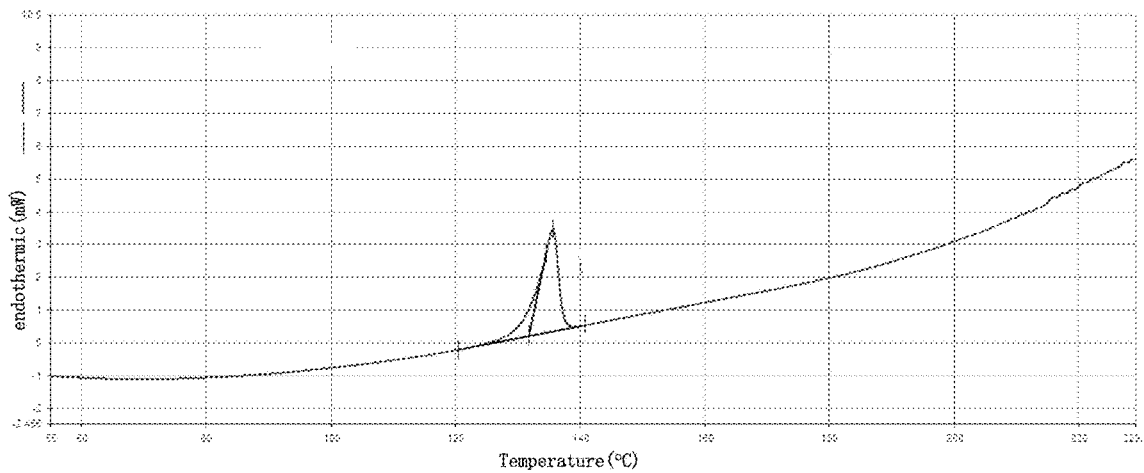
FIG. 4 is a differential scanning calorimetry (DSC) pattern of the crystal form A of the crystal of Example 1 of the present invention.

In another preferred embodiment, the crystal form A has a DSC pattern substantially as shown in FIG. 4.

5) the crystal form A has a hygroscopicity of less than 1%.

In another preferred embodiment, when relative humidity RH is less than 50%, the crystal form A has a hygroscopicity of less than 0.3%.

Figure 5:
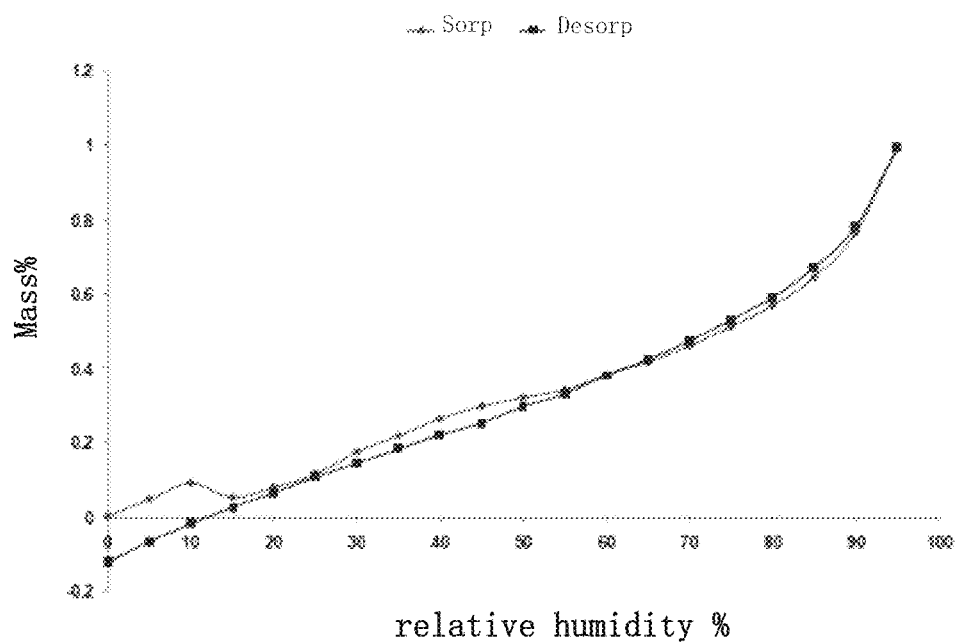
FIG. 5 is a hygroscopicity analysis (DVS) pattern of the crystal form A of the crystal of Example 1 of the present invention.

In another preferred embodiment, the crystal form A has a DVS pattern substantially as shown in FIG. 5.

In another preferred embodiment, IR pattern of the crystal form A includes following characteristic absorption peaks expressed by wavelength λ: 3368±2 cm$^{-1}$, 2940±2 cm$^{-1}$, 2848±2 cm$^{-1}$, 2222±2 cm$^{-1}$, 1729±2 cm$^{-1}$, 1672±2 cm$^{-1}$, 1564±2 cm$^{-1}$, 1529±2 cm$^{-1}$, 1470±2 cm$^{-1}$, 1454±2 cm$^{-1}$, 1387±2 cm$^{-1}$, 1298±2 cm$^{-1}$, 1203±2 cm$^{-1}$, 1105±2 cm$^{-1}$, 1075±2 cm$^{-1}$, 921±2 cm$^{-1}$, 781±2 cm$^{-1}$, 709±2 cm$^{-1}$.

In another preferred embodiment, the IR pattern of the crystal form A includes following characteristic absorption peaks expressed by wavelength λ: 3368, 2940, 2848, 2222, 1729, 1672, 1564, 1529, 1470, 1454, 1387, 1298, 1203, 1105, 1075, 921, 781, 709 cm$^{-1}$.

Figure 6:
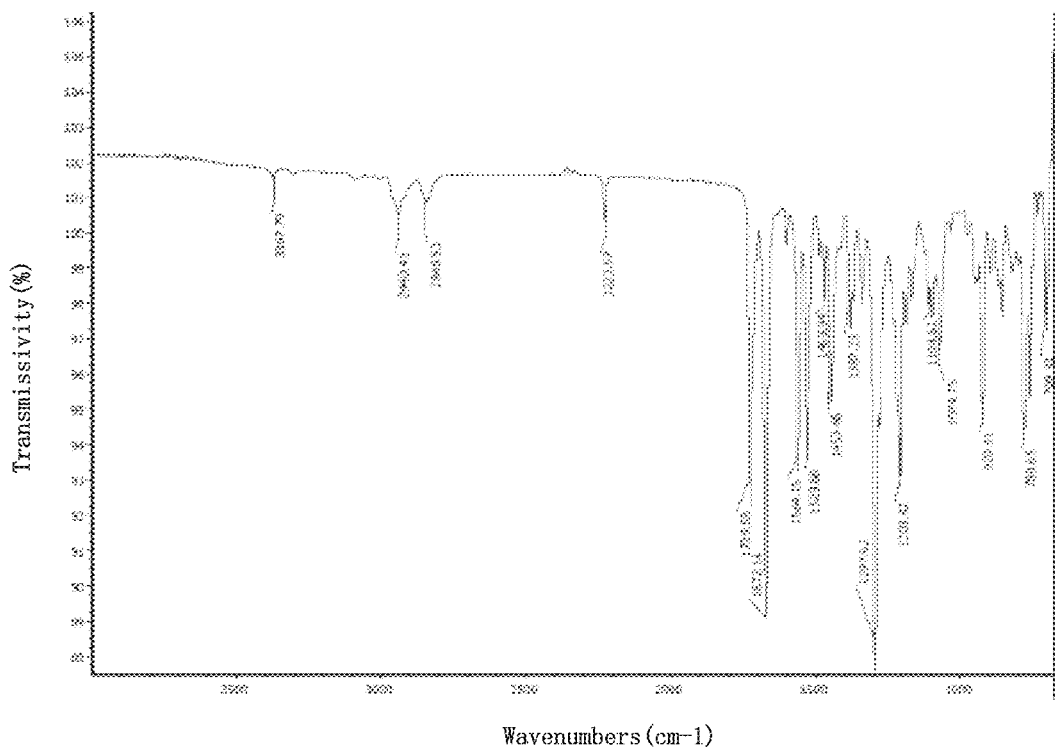
FIG. 6 is an infrared spectrum (IR) pattern of the crystal form A of the crystal of Example 1 of the present invention.

In another preferred embodiment, the crystal form A has an IR pattern substantially as shown in FIG. 6.

Figure 7:
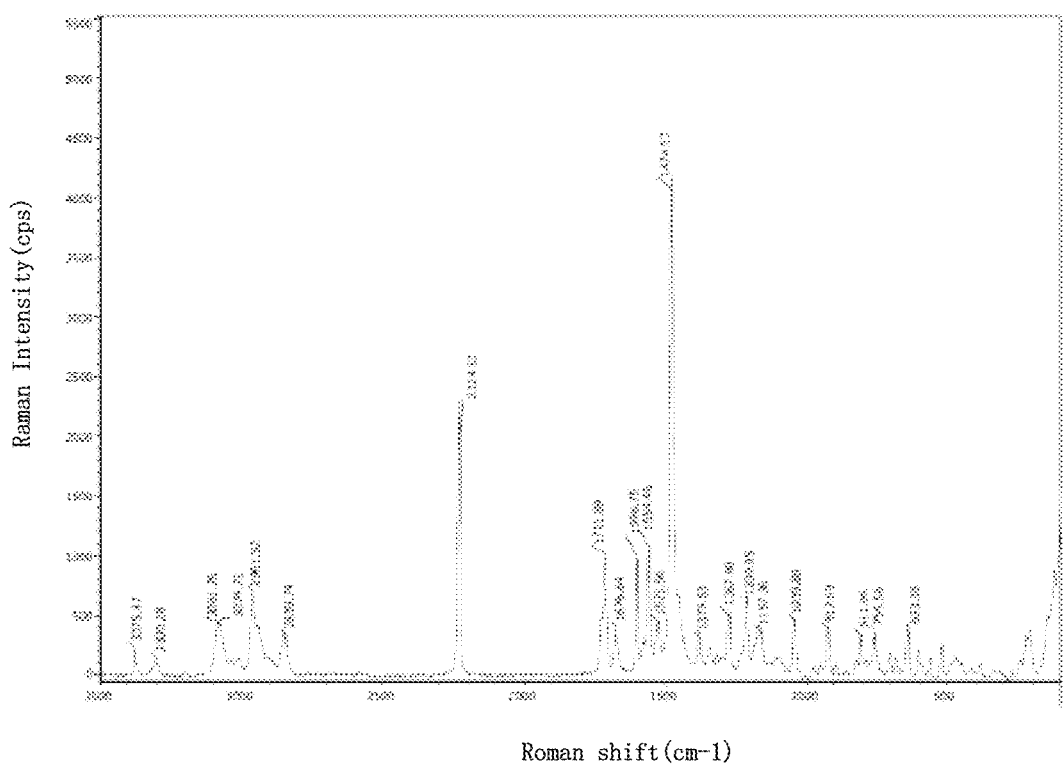
FIG. 7 is a Raman spectrum (Raman) pattern of the crystal form A of the crystal of Example 1 of the present invention.

In another preferred embodiment, the crystal form A has a Raman pattern substantially as shown in FIG. 7.

Compared with amorphous (R)-methyl-2-(3-aminopiperidin-1-yl)-3-(2-cyanobenzyl)-4-carbonyl-3,4-dihydrothiophene[3,2-d] pyrimidine-6-carboxylic acid powder, the crystal form A compound of the present invention orally administered has better hypoglycemic activity for prevention or treatment of type II diabetes, and the crystal form A can improve solubility of the compound, enhance oral absorption ability and improve bioavailability, and the crystal form A has a better effect in prevention or treatment of type II diabetes.

Crystal Composition

In the present invention, the crystal composition comprises a crystal of the crystal form A or is made from a crystal of the crystal form A.

In another preferred embodiment, the weight percentage of the crystal of the crystal form A is 60 to 99.999%, preferably 80 to 99.999%, more preferably 90 to 99.999%, based on total weight of the crystal composition.

In another preferred embodiment, the crystal composition further comprises: non-crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal and amorphous (R)-methyl-2-(3-aminopiperidin-1-yl)-3-(2-cyanobenzyl)-4-carbonyl-3,4-dihydrothiophene[3,2-d] pyrimidine-6-carboxylic acid.

Preparation Method for the Crystal Form A

In the present invention, it provides a method for preparing the crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal, and the method comprises following steps:

1) providing a first solution containing a first solvent and (R)-methyl-2-(3-aminopiperidin-1-yl)-3-(2-cyanobenzyl)-4-carbonyl-3,4-dihydrothiop hene[3,2-d] pyrimidine-6-carboxylic acid dissolved in the first solvent, wherein the first solvent is a good solvent and selected from the following group consisting of alcohols, ketones, esters, chlorinated alkanes, or combinations thereof;

In the present invention, the alcohols, the ketones and the esters are not particularly limited, which can be selected from conventional materials in the art, or may be prepared by conventional methods, or are commercially available.

Typically, the alcohols are C1-C10 alcohols, preferably C1-C8 alcohols, more preferably C1-C5 alcohols.

Typically, the alcohols include (but not limited to) methanol, ethanol, n-propanol, isopropanol, n-butanol, neopentyl alcohol, or combinations thereof.

Typically, the ketones are C2-C8 ketones, preferably C3-C5 ketones.

Typically, the ketones include (but not limited to) acetone, isobutanol butanone, or combinations thereof.

Typically, the esters are C1-C10 esters, preferably C1-C7 esters, more preferably C1-C5 esters.

Typically, the esters include (but not limited to) methyl formate, ethyl acetate, isobutyl formate, or combinations thereof.

Typically, the chlorinated alkanes include (but not limited to) dichloromethane, trichloromethane, or combinations thereof, preferably dichloromethane.

In another preferred embodiment, the (R)-methyl-2-(3-aminopiperidin-1-yl)-3-(2-cyanobenzyl)-4-carbonyl-3,4-dihydrothiop hene[3,2-d] pyrimidine-6-carboxylic acid is an amorphous compound.

2) adding a second solvent to the first solution to crystallize and give the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal, wherein the second solvent is a poor solvent and selected from the following group consisting of water, ethers, alkanes, tetrahydrofuran, 1,4-dioxane, or combinations thereof.

Typically, the ethers are C1-C10 ethers, preferably C1-C8 ethers, more preferably C1-C6 ethers.

Typically, the ethers include (but not limited to) petroleum ether, t-butyl methyl ether, diethyl ether, isopropyl ether, diethyl ether, or combinations thereof.

Typically, the alkanes are C2-C15 alkanes, preferably C3-C10 alkanes, more preferably C4-C8 alkanes.

Typically, the alkanes include (but not limited to) n-pentane, n-hexane, n-heptane, or combinations thereof.

In another preferred embodiment, after step 2), the method comprises the following step:

(3) filtering and/or drying the obtained solid in step (2), to give the crystal form A of (R)-methyl-2-(3-aminopiperidin-1-yl)-3-(2-cyanobenzyl)-4-carbonyl-3,4-dihydrothiop hene [3,2-d] pyrimidine-6-carboxylic acid crystal.

In the present invention, the drying conditions (such as temperature, pressure, time, etc.) are not particularly limited.

In another preferred embodiment, temperature for the drying is from 10 to 70° C., preferably from 20 to 80° C., more preferably from 25 to 40° C.

In another preferred embodiment, pressure for the drying is from 0 to 20 kPa, preferably from 0 to 10 kPa, more preferably from 5 to 10 kPa.

In another preferred embodiment, time for the drying is from 5 to 150 hours, preferably from 30 to 100 hours, more preferably from 60 to 80 hours.

In another preferred embodiment, yield for the method is from 50% to 99%, preferably from 75% to 99%, more preferably from 85% to 99%.

In the present invention, in the first solution, the concentration of the solute (R)-methyl-2-(3-aminopiperidin-1-yl)-3-(2-cyanobenzyl)-4-carbonyl-3,4-dihydrothiop hene[3,2-d] pyrimidine-6-carboxylic acid is 0.1 g/L to saturated concentration.

In another preferred embodiment, in the first solution, the concentration of the solute (R)-methyl-2-(3-aminopiperidin-1-yl)-3-(2-cyanobenzyl)-4-carbonyl-3,4-dihydrothiop hene [3,2-d] pyrimidine-6-carboxylic acid is 0.1 g/L to 100 g/L, preferably 1 g/L to 870 g/L, more preferably 10 g/L to 70 g/L, most preferably 10 g/L to 50 g/L.

In another preferred embodiment, in the first solution, the concentration of the solute (R)-methyl-2-(3-aminopiperidin-1-yl)-3-(2-cyanobenzyl)-4-carbonyl-3,4-dihydrothiop hene [3,2-d] pyrimidine-6-carboxylic acid is an unsaturated concentration.

Typically, the crystallization is carried out at 0-50° C.

In another preferred embodiment, the crystallization is carried out at 0 to 40° C., preferably 20 to 30° C.; preferably room temperature.

In another preferred embodiment, the time for the crystallization is not particularly limited, preferably is 0.05 to 72 hours (or more), preferably is 0.1 to 48 hours, more preferably is 1 to 24 hours, most preferably is 2 to 12 hours.

In another preferred embodiment, the crystallization is carried out with stirring.

Pharmaceutical Composition and Application

A pharmaceutical composition is provided in the present invention, comprising the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal and pharmaceutically acceptable excipients.

It should be understood that, in the present invention, the excipients are not particularly limited, which can be selected from conventional materials in the art, or may be prepared by conventional methods, or are commercially available.

Typically, the excipient includes (but not limited to) fillers, disintegrants, binders, lubricants, or combinations thereof.

Typically, the filler includes (but not limited to) starch, lactose, microcrystalline cellulose, dextrin, mannitol, magnesium oxide, calcium sulfate, or combinations thereof.

Typically, the disintegrant includes (but not limited to) carboxymethylcellulose and salts thereof, crosslinked carboxymethylcellulose and salts thereof, crosslinked povidone, sodium carboxymethyl starch, low substituted hydroxypropylcellulose, or combinations thereof.

Typically, the binder includes (but not limited to) povidone, hydroxypropylmethylcellulose, starch pulp, or combinations thereof.

Typically, the lubricant includes (but not limited to) magnesium stearate, calcium stearate, or combinations thereof.

A use of the crystal form A of (R)-methyl-2-(3-aminopiperidin-1-yl)-3-(2-cyanobenzyl)-4-carbonyl-3,4-dihydrothi ophene[3,2-d] pyrimidine-6-carboxylic acid crystal or the crystal composition or the pharmaceutical composition is also provided in the present invention, for preparation of a medicament for preventing or treating type II diabetes and/or complications of type II diabetes.

Typically, the complications of type II diabetes include (but not limited to) coronary artery disease, stroke, hypertension, nephropathy, peripheral vascular disease, neurological disease, and retinopathy.

A method for treating or preventing type II diabetes and/or complications of type II diabetes is also provided in the present invention by administering to a subject a therapeutically effective amount of the crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal or the crystal composition or the pharmaceutical composition.

The administration amount of the crystal form A of the present invention or the pharmaceutical composition thereof varies depending on age, sex, race and condition of the subject.

The compound of the present invention may be administered alone or in combination with other drugs or active ingredients.

In the present invention, the administration mode of the crystal form A or the pharmaceutical composition of the present invention, which is not particularly limited and can be the same as or similar to that of conventional (R)-methyl-2-(3-aminopiperidin-1-yl)-3-(2-cyanobenzyl)-4-carbonyl-3,4-dihydrothiop hene[3,2-d] pyrimidine-6-carboxylic acid, includes (but not limited to) oral, transdermal, intravenous, intramuscular, topical, and the like.

Compared with the prior art, the present invention has following main advantages:

(1) the crystal form A prepared by the method of the present invention has a higher purity;

(2) the crystal form A of the present invention has better stability, in particular thermal stability;

(3) the crystal form A of the present invention has a lower hygroscopicity, and when the relative humidity RH is less than 50%, the hygroscopicity of the crystal form A is less than 0.3%;

(4) the crystal form A of the present invention is not easily degradable under conventional conditions;

(5) The preparation method for the crystal form A of the present invention is simple, easy to control and reproducible, and is suitable for industrial production.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the recorded content can apply to the methods of the invention. The method of the preferred embodiment described herein and the material are only for demonstration purposes.

General Test Methods and Test Parameters

In the present invention, the crystal is subjected to a series of general tests as follows.

Powder X-ray Diffraction (XRD) is a structural analysis method for internal spatial distribution of atoms in material by using diffraction of X-ray formed by crystals. When X-rays having a certain wavelength are irradiated onto a crystalline substance, the X-rays are scattered due to the presence of a regularly arranged atom or ion inside the crystal, and the scattered X-rays are intensified in some directions, thereby showing unique diffraction phenomenon corresponding to crystalline structure.

In the present invention, the test parameters for XRD are as follows: Instrument type: Bruker D8advance; Target: Cu—K$_\alpha$ (40 kV, 40 mA); Distance from sample to detector: 30 cm; Scanning range: 3°~40° (2 theta value); Scanning speed: 0.1 s.

Thermo Gravimetric Analysis (TGA) is an analytical technique for determining the mass change of one material with temperature under program-controlled conditions. Thermo Gravimetric Analysis can be used to obtain the heat generated by the thermal changes of the sample. It is suitable for checking the process and value of the loss of crystal solvent or water molecules or the sublimation and decomposition of the sample in the crystalline material. It can also effectively distinguish whether the material contains crystal solvent or water.

In the present invention, the test parameters for TGA are as follows: Instrument type: Netzsch TG 209F3; Crucible: Alumina crucible; Temperature range: 30 to 400° C.; Scanning rate: 10 K/min; purge gas: 25 mL/min; Protective gas: 15 mL/min.

Differential Scanning calorimeter (DSC) is a technique for determining the change of heat difference between the sample and the inert reference (commonly use $\alpha$-Al$_2$O$_3$) with temperature by using program-controlled heating or cooling. DSC analysis is suitable for analyzing sample's states of such as the melting decomposition, mixed crystal, crystal transformation etc.

In the present invention, the test parameters for DSC are as follows: Instrument type: Perkin Elmer DSC 8500; Crucible: Aluminum crucible; Scanning from 50° C. to 280° C. at a heating rate of 10° C./min under nitrogen purge.

Raman Spectroscopy (RM) is a method of studying the molecular vibration based on the Raman effect. In contrast to the infrared absorption spectrum, the Raman Spectroscopy studies the frequency of the scattered light generated by the interaction of the molecule and the optical. Non-polar groups, which generally have unobvious infrared absorption, have obvious Raman spectra absorption.

In the present invention, the test parameters for RM are as follows: Instrument type: Thermo DXR Raman Microscope (confocal microscopy Raman spectrometer); laser wavelength: 532 nm; exposure time: 1.0 sec; exposure times: 10.

Infra-red Spectrometry (IR) is the first analytical method used for the recognition and identification of crystalline substances. Due to different electrical environment of covalent bond in different crystal molecules, the covalent bond strength may change, and the change of covalent bond strength will inevitably lead to different IR spectra of different crystal forms.

In the present invention, the test parameters for IR are as follows: Instrument type: Nicolet 6700 type Fourier transform infrared spectrometer; Single point ATR method with a resolution of 4.0 cm$^{-1}$.

Dynamic vapor absorption (DVS) test/water absorption test is conducted by rapidly measuring the increase and loss of the moisture in the sample caused by flow carrier gas with setted relative humidity (RH). The sample is placed on a digital microbalance with high sensitivity and high stability at a self-suspension state, and then by measuring the increase/decrease of the material mass so as to measure the adsorption/desorption of water vapor, thereby determining the hygroscopicity of the sample.

In the present invention, the test parameters for DVS are as follows: Instrument type: SMS DVS Intrinsic; Nonhydrate: 0 to 95%-0% RH; Temperature: 25° C.; Hydrate: 40 to 95%-0% RH; Temperature: 25° C.

EXAMPLE 1

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 1)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of ethanol, and 12 mL of petroleum ether was added, and under stirring at room temperature the crystallization was conducted until no more solid was precipitated and the crystallization time was about 2 hours. The obtained was filtered, and the resulting solid material was placed in a vacuum drying oven and vacuum dried for 70 hours at 25° C. under 5 KPa, to give 110 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

Result

The crystal form A of the crystal prepared in Example 1 was subjected to test such as polarization, XRD, TGA, DSC, DVS, IR and Raman etc.

FIG. 1 is a polarizing photograph of the crystal form A of the crystal of Example 1. It can be seen from FIG. 1 that the crystal form A is a powdery crystal.

FIG. 2 is an XRD pattern of the crystal form A of the crystal of Example 1. It can be seen from FIG. 2 that the crystal form A has absorption peaks at 5.42 Å, 7.25 Å, 8.09 Å, 8.87 Å, 14.18 Å, 15.59 Å, 16.65 Å, 17.84 Å, 19.03 Å, 20.01 Å, 20.67 Å, 21.72 Å, 21.95 Å, 22.49 Å, 24.53 Å, 25.18 Å, 25.56 Å, 27.47 Å, 28.61 Å, 33.09 Å, 34.25 Å, 37.86 Å.

FIG. 3 is a TG pattern of the crystal form A of the crystal of Example 1. It can be seen from FIG. 3 that the crystal form A has a weight loss of 77.65% at 210 to 400° C.

FIG. 4 is a differential scanning calorimetry (DSC) pattern of the crystal form A of the crystal of Example 1. It can be seen from FIG. 4 that the DSC corresponding to the crystal form A shows a melting point of 131.84° C.

FIG. 5 is a hygroscopicity analysis (DVS) pattern of the crystal form A of the crystal of Example 1. It can be seen from FIG. 5 that the crystal form A has a slight hygroscopicity, and in the range of conventional storage humidity, the variation range of humidity is small, smaller than 2.0%. Under 40% RH, the moisture content is 0.26%; under 65% RH, the moisture absorbed is 0.42%; under 80% RH, the moisture absorbed is 0.57%.

FIG. 6 is an infrared spectrum (IR) pattern of the crystal form A of the crystal of Example 1. It can be seen from FIG. 6 that the crystal form A has characteristic absorption peaks at 3368, 2940, 2848, 2222, 1729, 1672, 1564, 1529, 1470, 1454, 1387, 1298, 1203, 1105, 1075, 921, 781, 709 cm$^{-1}$.

FIG. 7 is a Raman spectrum (Raman) pattern of the crystal form A of the crystal of Example 1. It can be seen from FIG. 7 that the crystal form A has characteristic absorption peaks at 3375.5, 3300.3, 3081.8, 3074.7, 2961.9, 2839.7, 2224.1, 1711.9, 1676.6, 1596.8, 1554.5, 1521.6, 1474.6, 1373.5, 1267.8, 1209.1, 1157.4, 1039.9, 917.7, 812.0, 755.6, 633.4 cm$^{-1}$.

EXAMPLE 2

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 2)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of ethyl acetate, and 8 mL of petroleum ether was added, and under stirring at room temperature the crystallization was conducted until no more solid was precipitated. The obtained was filtered, and the resulting solid material was placed in a vacuum drying oven and vacuum dried for 70 hours at 25° C. under 5 KPa, to give 100 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

The XRD result of the obtained product was essentially the same as that of Example 1.

EXAMPLE 3

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 3)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of ethyl acetate, and 10 mL of diethyl ether was added, and under stirring at room temperature the crystallization was conducted until no more solid was precipitated. The obtained was filtered, and the resulting solid material was placed in a vacuum drying oven and vacuum dried for 70 hours at 25° C. under 5 KPa, to give 80 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

The XRD result of the obtained product was essentially the same as that of Example 1.

EXAMPLE 4

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 4)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of ethanol, and 10 mL of diethyl ether was added, and under stirring at room temperature the crystallization was conducted until no more solid was precipitated. The obtained was filtered, and the resulting solid material was placed in a vacuum drying oven and vacuum dried for 70 hours at 25° C. under 5 KPa, to give 60 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

The XRD result of the obtained product was essentially the same as that of Example 1.

EXAMPLE 5

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 5)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of acetone, and 10 mL of petroleum ether was added, and under stirring at room temperature the crystallization was conducted until no more solid was precipitated. The obtained was filtered, and the resulting solid material was placed in a vacuum drying oven and vacuum dried for 70 hours at 25° C. under 5 KPa, to give 80 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

The XRD result of the obtained product was essentially the same as that of Example 1.

EXAMPLE 6

Preparation of crystal form A of (R)-methyl-2-(3-aminopiperidin-1-yl)-3-(2-cyanobenzyl)-4-carbonyl-3,4-dihydrot hiophene[3,2-d] pyrimidine-6-carboxylic acid crystal (No. 6)

200 mg of (R)-methyl-2-(3-aminopiperidin-1-yl)-3-(2-cyanobenzyl)-4-carbonyl-3,4-dihydrothiop hene[3,2-d] pyrimidine-6-carboxylic acid was dissolved in 1 mL of dichloromethane, and 8 mL of petroleum ether was added, and under stirring at room temperature the crystallization was conducted until no more solid was precipitated. The obtained was filtered, and the resulting solid material was placed in a vacuum drying oven and vacuum dried for 70 hours at 25° C. under 5 KPa, to give 100 mg of crystal form A of (R)-methyl-2-(3-aminopiperidin-1-yl)-3-(2-cyanobenzyl)-4-carbonyl-3,4-dihydrothiop hene[3,2-d] pyrimidine-6-carboxylic acid crystal.

The XRD result of the obtained product was essentially the same as that of Example 1.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. Crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal of formula I, wherein XRD pattern of the crystal form A includes following characteristic absorption peaks expressed by crystal plane distance d: 8.87±0.2 Å, 14.18±0.2 Å, 20.67±0.2 Å, 25.18±0.2 Å, 28.61±0.2 Å

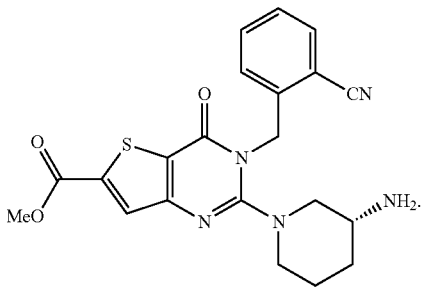

2. The crystal form A according to claim 1, wherein the XRD pattern of the crystal form A includes following characteristic absorption peaks expressed by crystal plane distance d: 7.25±0.2 Å, 8.09±0.2 Å, 8.87±0.2 Å, 14.18±0.2 Å, 16.65±0.2 Å, 20.67±0.2 Å, 21.95±0.2 Å, 25.18±0.2 Å, 28.61±0.2 Å.

3. The crystal form A according to claim 1, wherein, the crystal form A has one or more characteristics selected from the following group consisting of:
   1) TG pattern of the crystal form A has a characteristic absorption peak at 261±2° C.;
   2) TG pattern of the crystal form A has a characteristic absorption peak at 323±5° C.;
   3) the crystal form A has a heat weight loss of 77 to 78 wt % at 400° C.;
   4) DSC pattern of the crystal form A has a characteristic absorption peak at 135±5° C.;
   5) the crystal form A has a hygroscopicity of less than 1%.

4. A method for preparing the crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal according to claim 1, wherein the method comprises following steps:
   1) providing a first solution containing a first solvent and (R)-methyl-2-(3-aminopiperidin-1-yl)-3-(2-cyanobenzyl)-4-carbonyl-3,4-dihydrothiophene[3,2-d] pyrimidine-6-carboxylic acid dissolved in the first solvent, wherein
   the first solvent is a good solvent and selected from the following group consisting of alcohols, ketones, esters, chlorinated alkanes, or combinations thereof;
   2) adding a second solvent to the first solution to crystallize and give the crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal according to claim 1, wherein,
   the second solvent is a poor solvent and selected from the following group consisting of water, ethers, alkanes, tetrahydrofuran, 1,4-dioxane, or combinations thereof.

5. The method according to claim 4, wherein, in the first solution, the concentration of the solute (R)-methyl-2-(3-aminopiperidin-1-yl)-3-(2-cyanobenzyl)-4-carbonyl-3,4-dihydrothiophene[3,2-d] pyrimidine-6-carboxylic acid is 0.1 g/L to saturated concentration.

6. The method according to claim 4, wherein, the crystallization is carried out at 0 to 50° C.

7. A pharmaceutical composition, wherein the pharmaceutical composition comprises the crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid crystal according to claim 1 and pharmaceutically acceptable excipients.

8. A method for treating type II diabetes comprising administering to a subject a therapeutically effective amount of the crystal form A of (R)-methyl-2-(3-aminopiperidin-1-yl)-3-(2-cyanobenzyl)-4-carbonyl-3,4-dihydrothiophene[3,2-d] pyrimidine-6carboxylic acid crystal according to claim 1.

9. A method for treating type II diabetes comprising administering to a subject a therapeutically effective amount of the pharmaceutical composition according to claim 7.

* * * * *